(12) United States Patent
Davis et al.

(10) Patent No.: US 7,863,055 B2
(45) Date of Patent: Jan. 4, 2011

(54) SAMPLING SYSTEM FOR INTRODUCTION OF HIGH BOILING POINT STREAMS AT LOW TEMPERATURE

(75) Inventors: Dean Vinson Davis, Bartlesville, OK (US); Kenneth L. Gallaher, Bartlesville, OK (US); Eugene L. Kesselhuth, Bartlesville, OK (US); Jeffrey Scott Spaulding, Sunnyvale, CA (US)

(73) Assignee: Siemens Industry, Inc., Alpharetta, GA (US)

( * ) Notice: Subject to any disclaimer, the term of this patent is extended or adjusted under 35 U.S.C. 154(b) by 723 days.

(21) Appl. No.: 11/776,128

(22) Filed: Jul. 11, 2007

(65) Prior Publication Data

US 2008/0047324 A1    Feb. 28, 2008

Related U.S. Application Data

(62) Division of application No. 10/785,304, filed on Feb. 24, 2004, now Pat. No. 7,629,177.

(60) Provisional application No. 60/537,835, filed on Jan. 21, 2004.

(51) Int. Cl.
*G01N 33/00*    (2006.01)

(52) U.S. Cl. .............................. 436/181; 422/81; 422/99
(58) Field of Classification Search ................. 436/181; 422/81, 99
See application file for complete search history.

(56) References Cited

U.S. PATENT DOCUMENTS 6,670,608 B1 * 12/2003 Taylor et al. ................. 250/288

* cited by examiner

*Primary Examiner*—Sam P Siefke
(74) *Attorney, Agent, or Firm*—Filip A. Kowalewski

(57) ABSTRACT

The present invention is a method and apparatus for sampling a high-temperature gaseous process stream containing components with high boiling points. The sampling system is especially suited for instruments having extremely low pressure chambers, such as mass spectrometers. The invention reduces the condensation of high boiling point components of the sample in the sampling system without the necessity of maintaining extremely high temperatures. The gaseous sample is passed through an orifice from the high temperature stream into a lower-temperature zone of the sampling system where a low pressure is maintained by a vacuum pump. The low pressure reduces the boiling point of the sample components so they may be maintained in a gas phase without excessive heating. The low pressure sample is then introduced into an instrument chamber through a sample introduction valve.

16 Claims, 5 Drawing Sheets

SAMPLING SYSTEM FOR INTRODUCTION OF HIGH BOILING POINT STREAMS AT LOW TEMPERATURE

This is a divisional application of Ser. No. 10/785,304 filed on Feb. 24, 2004 now U.S. Pat. No. 7,629,177 and claims the benefit of U.S. Provisional Patent Application Ser. No. 60/537,835, filed Jan. 21, 2004 which is incorporated herein by reference.

FIELD OF THE INVENTION

The present invention relates generally to the field of sampling streams of gaseous materials for testing, and more particularly, to a method and apparatus for sampling process streams containing high-boiling-point components, without the need to maintain the sample at excessively high temperatures.

BACKGROUND OF THE INVENTION

Often when analyzing process streams using mass spectroscopy or other analysis techniques, the sampling system is the most important part of generating meaningful data. A properly functioning sampling system must withdraw a small amount of material from a process stream, and deliver it to an analysis instrument in a substantially intact condition.

In some process streams, for example acrylonitrile streams, there are small amounts of materials that boil at very high temperatures. Those components of the sample may condense out of the streams and plug the sampling lines. One frequently-used solution to that problem is to heat the sample stream to extremely high temperatures (180 degrees C.) to keep those components in the gas phase. That technique requires large amounts of energy and considerable expense. In some cases, the temperatures required are so high they cannot be reached using available equipment. Further, there may be materials present in the stream that decompose at such high temperatures, making such a solution impractical.

One example of a mass spectrometry sampling system that is heated to avoid condensation is shown in U.S. Pat. No. 3,944,824 to Chagney et al. That system samples gaseous compounds from a main process line, and includes a sampling line that is traced with steam to assure that no condensates reach the mass spectrometer.

U.S. Pat. No. 6,670,608 to Taylor et al. discloses a gas sampling system for sampling hazardous process gasses for analysis in an instrument that is remote from the process line. The technique uses a small-diameter capillary to transport a sample from the process stream to a mass spectrometer chamber. The capillary tube is open at one end to the high vacuum environment of the mass spectrometer chamber, and at the other end to the process stream. The capillary tube diameter is chosen based on the pressures in the sample stream and the mass spectrometer. A capillary tube heater is provided to maintain the sample in the capillary tube above boiling point.

It is known to control the temperature and pressure of a desolvation chamber when preparing a liquid sample for introduction into a mass spectrometer chamber. For example, in U.S. Pat. No. 4,403,147 to Melera et al., a jet stream of liquid droplets is sprayed through a probe into a low pressure, high temperature chamber for evaporation before entering the mass spectroscopy chamber.

There is therefore presently a need to provide a method and apparatus for sampling a process stream containing high-boiling-point gaseous components for analysis in a test instrument such as a mass spectrometer. Particularly, there is a need for a technique that can prevent condensation of the high-boiling-point components in the sampling system without excessively heating the sample. To the inventors' knowledge, no such technique is currently available.

SUMMARY OF THE INVENTION

The present invention addresses the needs described above by providing a method for sampling a high temperature process stream, without permitting high-boiling-point components to condense in the sampling system, and without requiring excessive heating. In one embodiment, the method includes the steps of evacuating a low temperature zone of a sampling system using a vacuum pump, admitting a portion of the high temperature process stream into the low temperature zone through an orifice, maintaining a stable vacuum pressure in the low temperature zone, and introducing a sample from the low temperature zone of the sampling system into test equipment through a sample introduction valve.

The orifice may have a diameter of between 0.005 inches and 0.025 inches. The step of maintaining a stable vacuum pressure in the low temperature zone may include metering an inlet of the vacuum pump, or may include controlling the vacuum pump.

The temperature of the high temperature process stream may be above a boiling point of a target sample component at the process stream pressure. The method may include the step of maintaining a temperature of the low temperature zone above a boiling point of a target sample component at the stable vacuum pressure.

The test equipment may include a mass spectrometer, and may be a FT-ICR mass spectrometer. The stable vacuum pressure may be a pressure between a pressure of the process stream and a high vacuum pressure of a vacuum chamber of the test equipment.

In another embodiment of the invention, a sampling system is provided for sampling a high temperature process stream to be tested in an analytical instrument. The sampling system includes an evacuation system for maintaining a low temperature zone of the sampling system at a vacuum pressure, a nozzle having an orifice connecting the sample stream with the low pressure zone of the sampling system, and a sample introduction valve connecting the low temperature zone of the sampling system with a vacuum chamber of the analytical instrument. The sample introduction valve is located between the evacuation system and the nozzle.

The analytical instrument may be a mass spectrometer and may be a FT-ICR mass spectrometer. The evacuation system may include a vacuum pump, and may further comprise a metering valve for metering an intake of the vacuum pump.

The orifice may have a diameter of between 0.005 inches and 0.025 inches.

Another embodiment of the invention is a method for sampling from a gaseous process stream at a process stream temperature and pressure. The subject stream has at least one component with a first boiling point lower than the process stream temperature when at the process stream pressure.

The method includes admitting a gas sample from the process stream through an orifice into a sampling system. The sampling system has a sampling system temperature lower than the first boiling point. The sampling system further has a sampling system pressure lower than the process stream pressure. The component in the gas sample thus has a second boiling point at the sampling system pressure, the second boiling point being lower than the sampling system temperature. The method also includes the step of introducing a portion of the gas sample into a test instrument chamber.

The step of introducing the portion of the gas sample into the test instrument chamber may include pulsing a piezoelectric valve. The method may also include the step of maintaining a stable vacuum pressure in the sampling system.

The step of maintaining a stable vacuum pressure in the sampling system may include regulating a vacuum pump throughput, and may include regulating a valve that meters flow through a vacuum pump.

DESCRIPTION OF THE INVENTION

The method and apparatus of the present invention provide a sampling system that can be maintained at a relatively low temperature without permitting condensation of the sample. To accomplish that, the inventors have developed a sampling system that utilizes the well-known principle that the boiling point of a liquid decreases with the pressure of the surrounding gasses. By lowering the pressure of the sample stream, problem materials boil at much lower temperatures. Those problem materials that tend to condense in the sampling system under ambient pressure will remain in the gaseous phase without the necessity of applying excessive heat to the sampling system.

In one example, a material that boils at 336 degrees C. at atmospheric pressure boils at about 140 degrees C. at 1 torr, boils at 90 degrees C. at 50 millitorr and boils at 70 degrees C. at 10 millitorr. Significant gains may therefore be made by lowering the pressure of the sampling system.

The sample is delivered to the instrument without substantial condensate and at a pressure lower than ambient pressure. The present invention is particularly effective in applications involving instruments that sample at sub-ambient pressures, such as a mass spectrometer.

Figure 1:
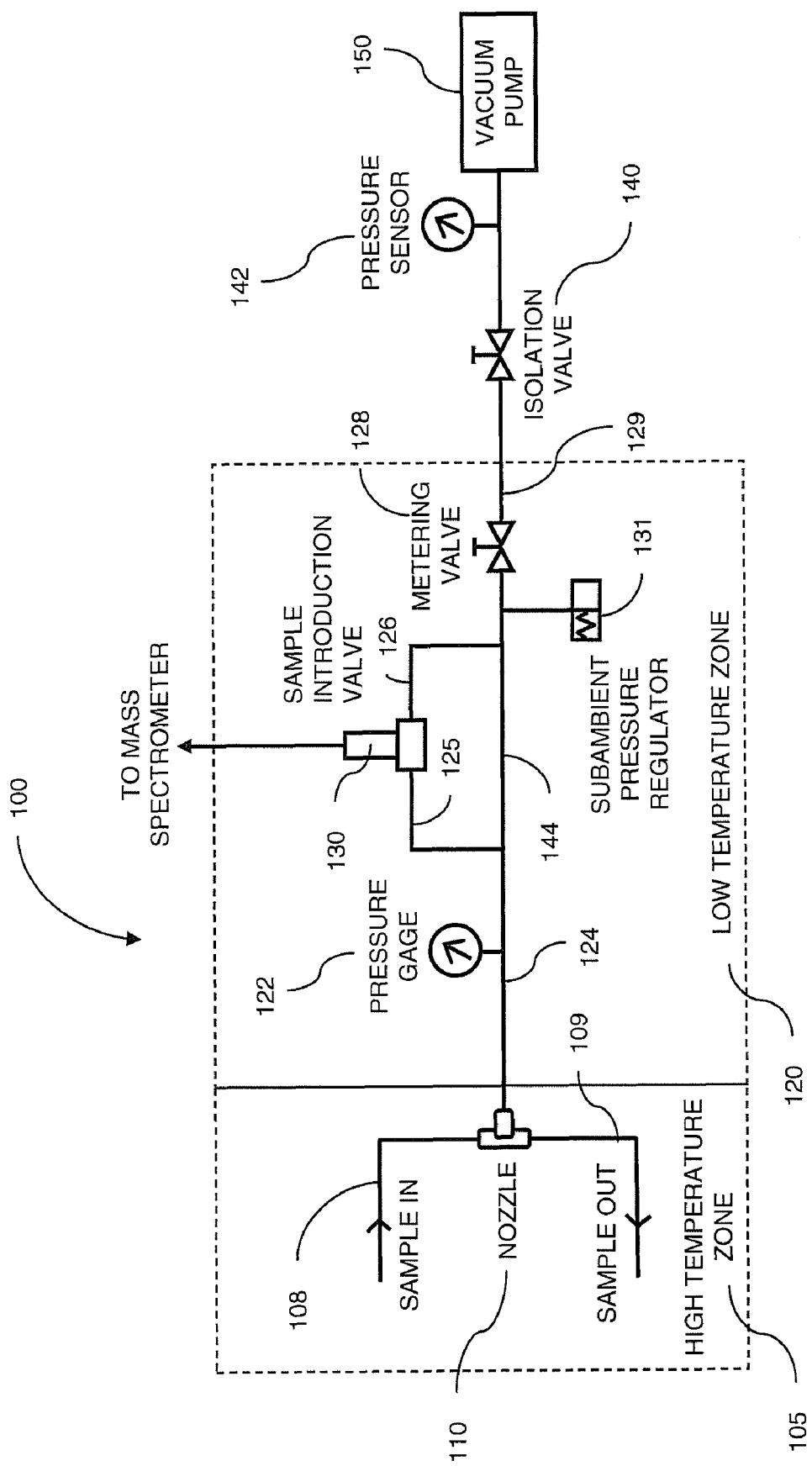
FIG. 1 is a schematic diagram showing the functional elements of a sampling system according to one embodiment of the invention.

A sampling system 100 according to the present invention is shown schematically in FIG. 1. The process gas is sampled either directly from a main process line (not shown) or from sampling return lines 108, 109 providing gas to the sampling system 100 from the main process line. In the exemplary prototype embodiment of the invention described herein, the sampling line 108 and return line 109 are ¼ inch tubing. It should be recognized that while the invention is described herein as a prototype constructed of individual components connected by tubing, an integral construction or a hybrid construction may be used without departing from the intended scope of the invention.

The sampling line 108 and return line 109 are in a high temperature zone 105 of the sampling system. The high temperature zone 105 is maintained at a temperature sufficiently high to keep all sample components in a gaseous state. The sample passes through the lines 108, 109 at a process pressure that may be atmospheric pressure or slightly above atmospheric pressure, as required by the process at the point where the sample is withdrawn.

A nozzle 110 having a small orifice is provided in the branch line 108 for permitting a small amount of the process gas to enter the low temperature zone 120 of the sampling system. A pressure at the downstream side of the nozzle 110 and throughout the low temperature zone of the sampling system is maintained by a vacuum pump 150. The pressure in the low temperature zone is lower than the process stream pressure in lines 108, 109. The pressure in the low temperature zone is furthermore higher than a pressure in the mass spectrometer chamber being supplied by the sampling system.

In the prototype system constructed by the inventors, a ¼ inch tube 124 was used on the downstream side of the nozzle. That tube was reduced to 1/16 inch tubing 125 into the sample introduction valve and 1/16 inch tubing out of that valve. ¼ inch tubing 129 was used in the remainder of the low temperature zone 120.

A bypass path 144 is provided in parallel to the sample introduction valve. The bypass path is constructed of ¼ inch tubing. The bypass path 144 reduces restriction, permitting a larger orifice to be used to prevent clogging. The relative diameters of the bypass path (¼ inch) and the tubing to and from the sample introduction valve (1/16 inch) result in proper flow allocation between the two paths. Alternatively, a metering valve (not shown) may be used in the bypass path.

The vacuum pump 150 is preferably a positive displacement pump such as piston or vane-type vacuum pump. In an exemplary embodiment of the invention, the pressure in the low temperature zone is approximately 10 torr. One skilled in the art will recognize that other sampling system pressures may be selected based on the pressures of the process stream and the analysis chamber, and on the phase diagram characteristics of the gaseous components to be sampled. The vacuum pump preferably exhausts to an abatement system such as an atmospheric scrubber, as is known in the art.

An auxiliary heater (not shown) is provided in the low temperature zone to maintain a temperature in that zone that is sufficient to keep the components of the sample in a gas phase at the reduced pressure. Advantageously, that temperature is considerably lower than the temperature required to maintain a gas phase of those components at ambient pressure.

The pressure in the low temperature zone of the sampling system is maintained at a stable level by regulating a volumetric rate of the vacuum pump 150 and/or adjusting a flow rate of a metering valve 128 placed on the inlet side of the vacuum pump. The metering valve may alternatively be placed at the exhaust of the vacuum pump. In the prototype embodiment of the invention constructed by the inventors, the metering valve was adjusted manually with reference to a pressure gage 122. That adjustment may be automated through the use of a feedback control system.

An isolation valve 140 and a pressure sensor 142 are installed in-line near the vacuum pump for start-up and maintenance. A sub-ambient pressure regulator 131 may be installed in the low temperature zone to assist in maintaining a stable pressure at the sampling valve 130

A sample introduction valve 130 is provided for introducing an amount of the sample into the analysis chamber. In the case of a Fourier transform ion cyclotron resonance (FT-ICR) mass spectrometer, the preferred sample introduction valve is a piezoelectric pulse valve. Sample introduction valves operating on other principles may be use in conjunction with other analysis systems.

In the case of an FT-ICR mass spectrometer, the sample is introduced into a chamber evacuated to a pressure of about $10^{-10}$ torr. While it is necessary that the pressure in the sampling system be substantially greater than that in the MS chamber, it can be seen that there is a large pressure range between the process stream pressure (approximately 1 atmosphere=760 torr) and the MS chamber pressure of $10^{-10}$ torr. A pressure in the sampling system may therefore be selected based on the gaseous components present in the sample, and a desired maximum boiling point of those components.

Figure 3:
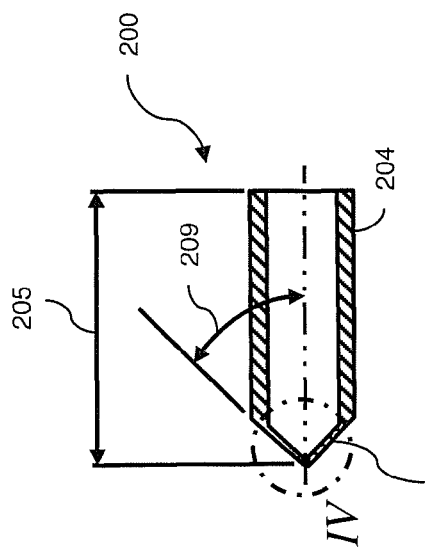
FIG. 3 is a sectional view of the nozzle of FIG. 2, taken through line III-III.
Figure 4:
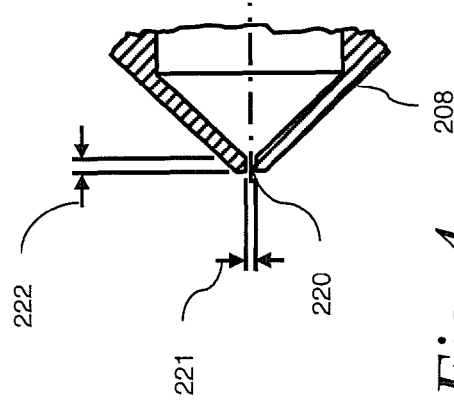
FIG. 4 is a detail view IV of the nozzle of FIG. 3.
Figure 2:
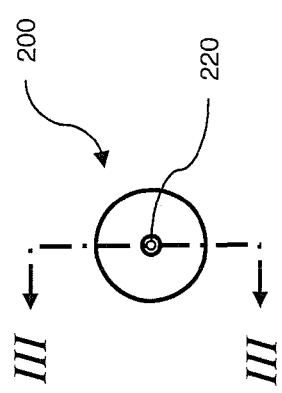
FIG. 2 is an end view of a nozzle used in accordance with one embodiment of the invention.

A nozzle fitting 200 according to one embodiment of the invention is shown in FIGS. 2, 3 and 4. The nozzle fitting 200 is inserted into a manifold through which the process stream passes.

The nozzle 200 is of generally cylindrical construction, having a wall 204 with a thickness of about 1/16 inches and a length 205 of about 1 inch. One end of the cylinder is open, while the other has a conical wall 208 with a cone angle 209 of about 45 degrees.

As best shown in FIG. 4, an orifice 220 is provided at the center of the conical wall 208. The orifice passes through a wall approximately 0.020 inches in thickness. In the prototype embodiment of the invention discussed herein, orifices having diameters of 0.010, 0.014 and 0.018 inches were tested with good results. In practice, the orifice size 221 is selected based on the desired pressure drop between the process stream and the sampling system, and also based on a trial and error determination of the effect of the orifice size on clogging and fouling.

Figure 5:
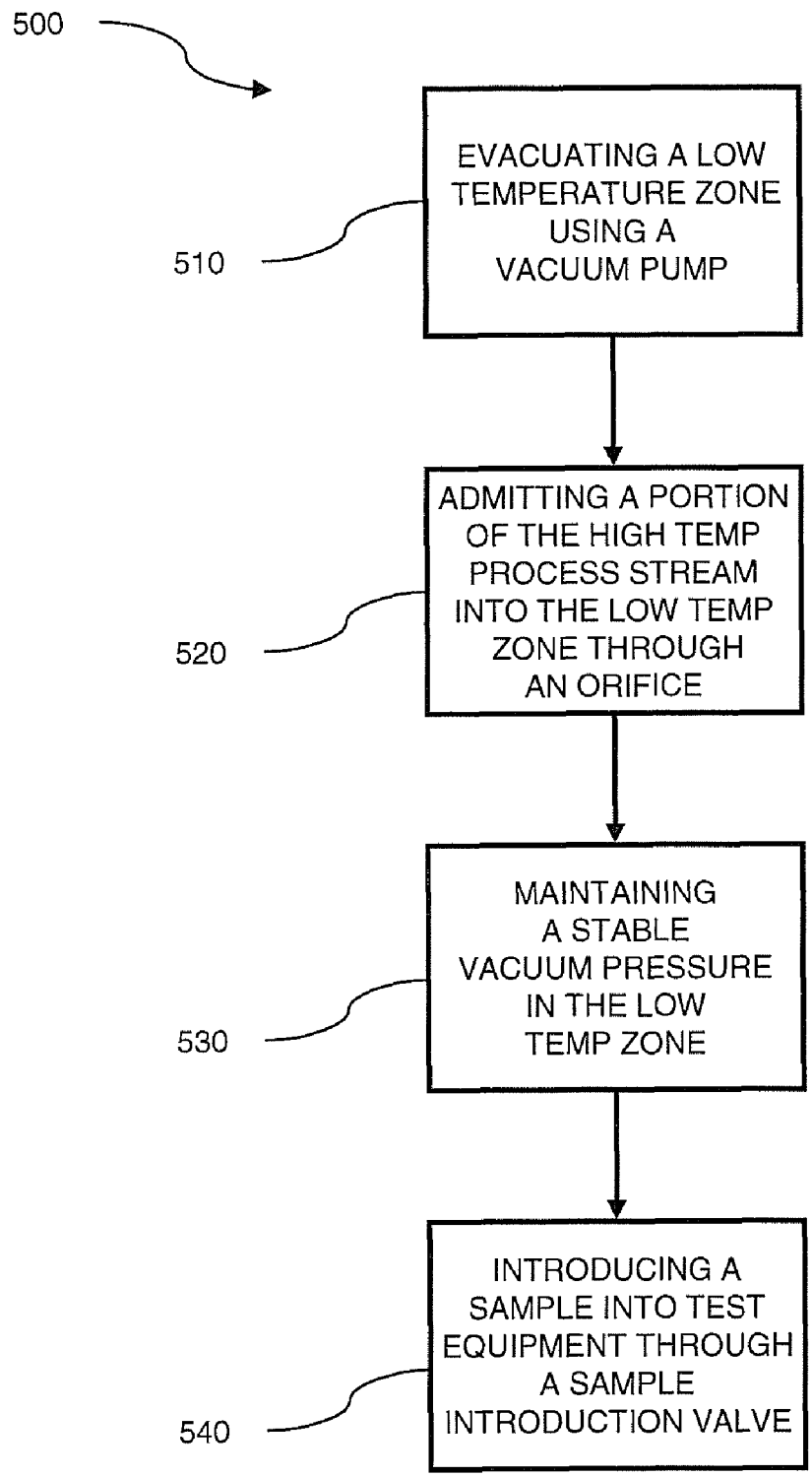
FIG. 5 is a block diagram showing a method of sampling a process stream according to one embodiment of the invention.

A method 500 for sampling a process stream in accordance with the invention is shown in block diagram form in FIG. 5. The method includes first evacuating (step 510) a low temperature zone of the sampling system using a vacuum pump. The term "evacuate" as used herein means to reduce a pressure in a vessel to a level below atmospheric pressure, but not necessarily to remove all contents from the vessel. As noted above, a mechanical, positive displacement vacuum pump such as a piston pump, vane pump or rotary pump is used. The sampling system is evacuated independently of the test instrument chamber, using a separate vacuum pump. In the case of an FT-ICR mass spectrometer, high vacuum is maintained in the test instrument chamber using a molecular pump such as a sputter ion pump. Initial vacuum for the instrument is drawn off-line using a mechanical pump.

A portion of the high temperature process stream is then admitted (step 520) into the low temperature zone through an orifice. As noted, the orifice diameter is selected based on the relative pressures of the sample system and the process stream, and on the clogging characteristics of the sample. A stable vacuum pressure is maintained (step 530) in the low temperature zone. The pressure may be maintained by controlling the vacuum pump, a metering valve, or both. By controlling the nozzle size and the amount of pumping, a stable pressure over a very wide range from millitorr to torr values can be reached and maintained at the sample introduction valve.

A sample is then introduced (step 540) from the low temperature zone of the sampling system into a test equipment chamber through the sample introduction valve. In the case where the instrument is a FT-ICR mass spectrometer, the sample introduction valve is a piezoelectric pulse valve that can admit extremely small quantities of material at precise points in time.

Figure 6:
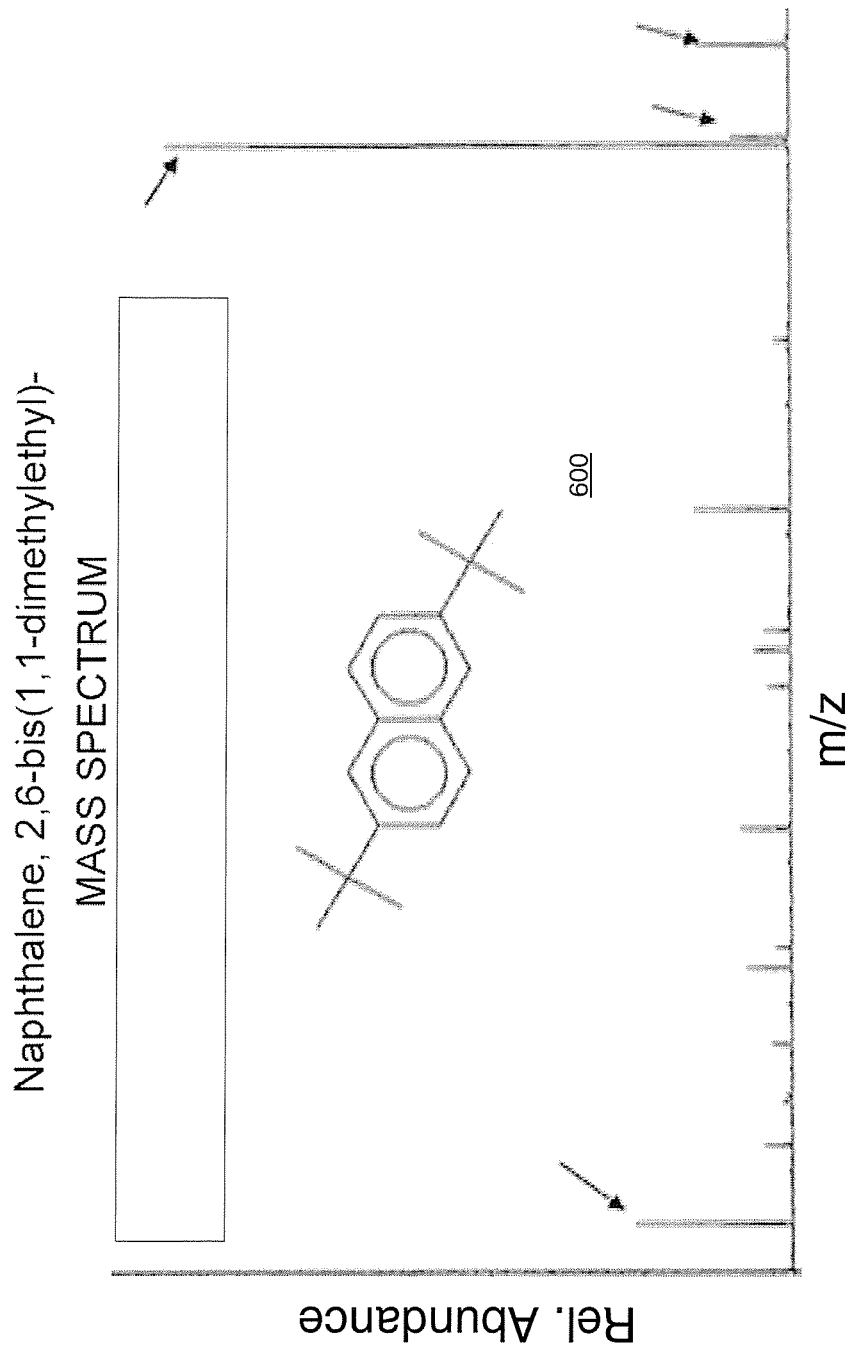
FIG. 6 is a sample mass spectrum obtained using a method and apparatus according to the invention.
Figure 7:
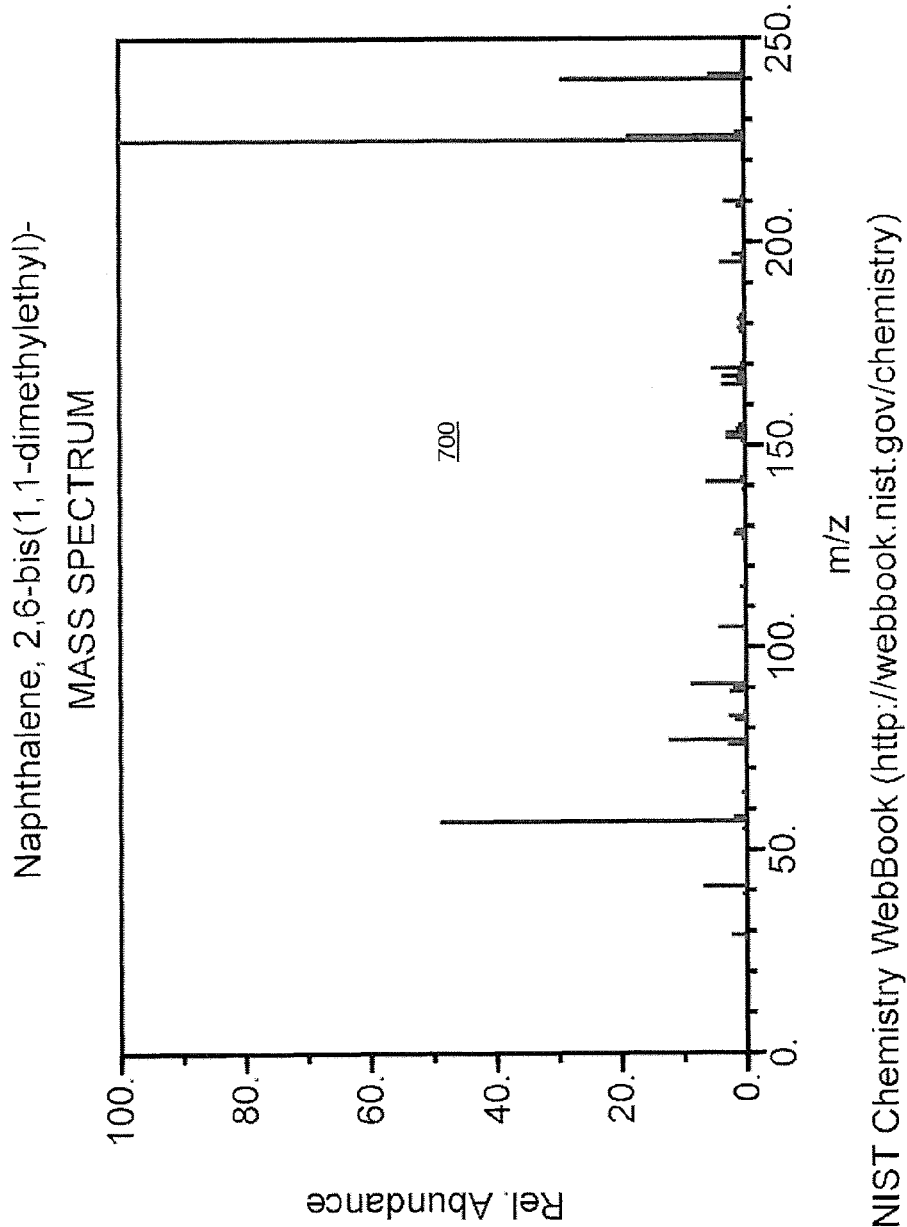
FIG. 7 is a reference mass spectrum of the same material analyzed in the spectrum of FIG. 6.

The prototype system discussed above was successfully used by the inventors to analyze dibutylnaphthalene, a high-boiling-point material that would likely cause clogging problems in atmospheric pressure sampling systems. The analysis was carried out using a FT-ICR mass spectrometer. A resulting mass spectrum from that experiment is presented in FIG. 6. A reference mass spectrum of the same material is shown in FIG. 7.

The analysis of dibutylnaphthalene was undertaken by placing the pure material in metal cylinder that was present in the high temperature region of a prototype sampling system of the invention. The high temperature zone 105 (FIG. 1), including the cylinder (not shown), was maintained at about 170 degrees C. A flow of nitrogen was passed through the cylinder at about 10 ml/minute. The low temperature zone 120 of the sampling system was held at 120 degrees C. The vacuum pump 150 was switched on and the metering valve 128 was adjusted until a stable pressure of about 10 torr was attained in the low temperature zone. The sample introduction valve 130 was then pulsed to admit a portion of the sample gas contained in the low temperature region. The spectrum 600 shown in FIG. 6 was generated. It can be seen that that spectrum correlates with the reference spectrum 700 shown in FIG. 7. The system was run for 30 minutes without any signs of plugging or clogging.

The foregoing Detailed Description is to be understood as being in every respect illustrative and exemplary, but not restrictive, and the scope of the invention disclosed herein is not to be determined from the Description of the Invention, but rather from the Claims as interpreted according to the full breadth permitted by the patent laws. For example, while the sampling method is described primarily for use in connection with a FT-ICR mass spectrometer, the technique of the invention may be used as a sampling means for other analysis instruments having a low pressure chamber into which the sample must be introduced, while remaining within the scope of the invention. It is to be understood that the embodiments shown and described herein are only illustrative of the principles of the present invention and that various modifications may be implemented by those skilled in the art without departing from the scope and spirit of the invention.

What is claimed is:

1. A sampling system for sampling a process stream to be tested in an analytical instrument, the sampling system comprising:
   a first fluid line containing a process stream having a first pressure;
   a second fluid line having a second pressure lower than the first pressure;
   an evacuation system coupled to the second line, for maintaining the second pressure;
   a nozzle having an orifice coupled between the first and second fluid lines, and establishing fluid communication there between; and
   a sample introduction valve coupled to the second line between the evacuation system and the nozzle, the sample introduction valve in communication with an analytical instrument having a chamber pressure lower than the second pressure.

2. The sampling system of claim 1, wherein the analytical instrument is a mass spectrometer.

3. The sampling system of claim 1, wherein the analytical instrument is an FT-ICR mass spectrometer.

4. The sampling system of claim 1, wherein the evacuation system comprises a vacuum pump.

5. The sampling system of claim 4, further comprising a metering valve, connected to the vacuum pump.

6. The sampling system of claim 1, wherein the orifice has a diameter of between 0.005 inches and 0.025 inches.

7. A sampling system for sampling a process stream, the sampling system comprising:
a first fluid line coupling a process stream having a pressure and a second fluid line;
means for evacuating the second fluid line to a vacuum pressure lower than the process stream pressure;
means for admitting a portion of the process stream from the first fluid line into the the second fluid line, in fluid communication with both lines;
means for maintaining a stable vacuum pressure in the second fluid line, the means for maintaining connected to the means for evacuating; and
means for introducing a sample from the second line into test equipment, the means for introducing connected to the second line downstream the means for admitting.

8. The sampling system of claim 7, wherein the means for admitting comprises a nozzle.

9. The sampling system of claim 8 wherein the nozzle comprises an orifice having a diameter of between 0.005 inches and 0.025 inches.

10. The sampling system of claim 7, wherein the means of maintaining a stable vacuum pressure in the low temperature zone comprises a metering valve.

11. The sampling system of claim 7, wherein the means for maintaining a stable vacuum pressure in the low temperature zone comprises a pressure regulator.

12. The sampling system of claim 7, wherein the means for evacuating comprises a vacuum pump.

13. The sampling system of claim 7, further comprising a heater connected to the means for admitting for maintaining a temperature in the second line above a boiling point of a target sample component at the stable vacuum pressure.

14. The sampling system of claim 7, further comprising a mass spectrometer connected to the means for introducing a sample.

15. The sampling system of claim 7, further comprising a FT-ICR mass spectrometer connected to the means for introducing a sample.

16. The sampling system of claim 7, wherein the means for evacuating comprises a first vacuum pump and wherein the test equipment comprises a mass spectrometer and further comprising a second vacuum pump, the second vacuum pump connected to a chamber of the mass spectrometer for evacuating the chamber to a pressure lower than the stable vacuum pressure in the second fluid line.

* * * * *